United States Patent
Okano et al.

(10) Patent No.: US 10,288,719 B2
(45) Date of Patent: May 14, 2019

(54) OBJECT INFORMATION ACQUIRING APPARATUS AND INFORMATION PROCESSING APPARATUS

(71) Applicant: CANON KABUSHIKI KAISHA, Tokyo (JP)

(72) Inventors: Mie Okano, Moriya (JP); Yohei Hashizume, Tokyo (JP); Yasufumi Asao, Atsugi (JP)

(73) Assignee: CANON KABUSHIKI KAISHA, Tokyo (JP)

(*) Notice: Subject to any disclaimer, the term of this patent is extended or adjusted under 35 U.S.C. 154(b) by 271 days.

(21) Appl. No.: 15/426,247

(22) Filed: Feb. 7, 2017

(65) Prior Publication Data

US 2017/0242096 A1 Aug. 24, 2017

(30) Foreign Application Priority Data

Feb. 24, 2016 (JP) ................................ 2016-033354

(51) Int. Cl.
*G01S 5/18* (2006.01)
*A61B 5/00* (2006.01)
*A61B 34/20* (2016.01)
*A61B 90/00* (2016.01)

(52) U.S. Cl.
CPC ............. *G01S 5/18* (2013.01); *A61B 5/0046* (2013.01); *A61B 5/0095* (2013.01); *A61B 34/20* (2016.02); *A61B 2034/2051* (2016.02); *A61B 2034/2055* (2016.02); *A61B 2090/049* (2016.02)

(58) Field of Classification Search
CPC ......... G01S 5/18; A61B 34/20; A61B 5/0046; A61B 5/0095; A61B 2034/2055; A61B 2034/2051; A61B 2090/049
See application file for complete search history.

(56) References Cited

U.S. PATENT DOCUMENTS

| | | | |
|---|---|---|---|
| 7,864,307 B2 | 1/2011 | Fukutani et al. | 356/73 |
| 8,864,667 B2 | 10/2014 | Asao et al. | 600/437 |
| 9,116,111 B2 | 8/2015 | Nakajima et al. | G01N 29/2418 |
| 2010/0087733 A1 | 4/2010 | Nakajima et al. | 600/437 |
| 2013/0217995 A1 | 8/2013 | Kruger | 600/407 |
| 2016/0022149 A1 | 1/2016 | Asao et al. | A61B 5/0095 |
| 2016/0091415 A1 | 3/2016 | Furukawa et al. | G01N 21/1702 |

(Continued)

FOREIGN PATENT DOCUMENTS

| | | | | |
|---|---|---|---|---|
| CN | 107115097 A | * | 9/2017 | ............ A61B 5/0046 |
| JP | 2017148230 A | * | 8/2017 | ............ A61B 5/0046 |

*Primary Examiner* — Daniel Pihulic
(74) *Attorney, Agent, or Firm* — Venable LLP

(57) ABSTRACT

An object information acquiring apparatus, comprises a light irradiating unit configured to irradiate an object with light; a probe configured to receive an acoustic wave generated from the object and convert into an electrical signal; a characteristic information acquiring unit configured to acquire characteristic information relating to the object based on the electrical signal; an area information acquiring unit configured to acquire information relating to a reachable area of the light; a location detecting unit configured to acquire an operator location; and a determining unit configured to determine whether the operator location is in a first state where the operator location overlaps with the reachable area of the light or a second state where the operator location does not overlap with the reachable area of the light.

16 Claims, 8 Drawing Sheets

(56) References Cited

U.S. PATENT DOCUMENTS

| | | |
|---|---|---|
| 2017/0055844 A1 | 3/2017 | Umezawa et al. ... A61B 5/0095 |
| 2017/0095155 A1 | 4/2017 | Nakajima et al. ............ 600/323 |
| 2017/0242096 A1* | 8/2017 | Okano ................. A61B 5/0046 |

* cited by examiner

OBJECT INFORMATION ACQUIRING APPARATUS AND INFORMATION PROCESSING APPARATUS

BACKGROUND OF THE INVENTION

Field of the Invention

The present invention relates to an object information acquiring apparatus for acquiring information on an object.

Description of the Related Art

Object information acquiring apparatuses for acquiring information on an object include photographing apparatuses using positron emission tomography (PET), single-photon emission computed tomography (CT), and X-rays. Since such apparatuses use high-energy electromagnetic waves including radioactive rays and present a risk of radiation exposure, measures must be taken involving, for example, having an operator (a physician, a technician, or the like) relocate to another room during photography or having only an examinee enter the apparatus to undergo photography. Therefore, there are cases where immediate attention cannot be given to an examinee experiencing anxiety or feeling unwell. Against this background, a medical apparatus is desired which enables an operator to be present by an examinee's side during photography and which does not pose a burden on the operator.

Meanwhile, ultrasonic apparatuses are known as diagnostic apparatuses which are noninvasive to an object and, in particular, apparatuses using photoacoustic tomography (PAT) are attracting attention. PAT refers to an apparatus which, by irradiating an object with light such as laser light, receives acoustic waves generated from the object and acquires information on the object as image information. Since PAT uses light instead of radioactive rays to acquire object information, an operator and an examinee can be present in a same space during photography (refer to US Patent Application Publication No. 2013/0217995 (Specification)).

SUMMARY OF THE INVENTION

Since PAT uses high-output laser light, care must be taken to avoid irradiating parts other than a measurement object with the laser light. For example, an upper limit value of an intensity of light with which a human body can be irradiated is defined as maximum permissible exposure (MPE). Therefore, irradiation of parts other than a measurement object part on an object by light must be suppressed to the greatest extent feasible.

However, with conventional apparatuses including the apparatus described in US Patent Application Publication No. 2013/0217995 (Specification), there is a risk that a gap may be created between an object and the apparatus when the object moves during measurement and, consequently, laser light leaks into space.

The present invention has been made in consideration of such problems existing in prior art and an object thereof is to provide an object information acquiring apparatus capable of suppressing irradiation of laser light outside of an object.

The present invention in its one aspect provides an object information acquiring apparatus, comprising a light irradiating unit configured to irradiate an object with light; an acoustic probe configured to receive an acoustic wave generated from the object due to the light and to convert the acoustic wave into an electrical signal; a characteristic information acquiring unit configured to acquire characteristic information relating to the object based on the electrical signal; an area information acquiring unit configured to acquire information relating to a reachable area of the light irradiated from the light irradiating unit; a location detecting unit configured to acquire an operator location which is a location of an operator; and a determining unit configured to determine whether the operator location is in a first state where the operator location overlaps with the reachable area of the light or a second state where the operator location does not overlap with the reachable area of the light.

The present invention in its another aspect provides a control method for an object information acquiring apparatus including a light irradiating unit which irradiates an object with light and an acoustic probe which receives an acoustic wave generated from the object due to the light and which converts the acoustic wave into an electrical signal, the control method comprising acquiring characteristic information relating to the object, based on the electrical signal; acquiring information relating to a reachable area of the light irradiated from the light irradiating unit; acquiring an operator location which is a location of an operator; and determining whether the operator location is in a first state of where the operator location overlaps with the reachable area of the light or a second state where the operator location does not overlap with the reachable area of the light.

The present invention in its another aspect provides an information processing apparatus which determines whether or not to permit irradiation of an object with light by an object information acquiring apparatus, the information processing apparatus comprising an area information acquiring unit configured to acquire information relating to a reachable area of the light with which the object is irradiated; a location detecting unit configured to acquire an operator location which is a location of an operator of the object information acquiring apparatus; and a determining unit configured to determine whether the operator location is in a first state where the operator location overlaps with the reachable area of the light or a second state where the operator location does not overlap with the reachable area of the light.

According to the present invention, an object information acquiring apparatus capable of suppressing irradiation of laser light outside of an object can be provided.

Further features of the present invention will become apparent from the following description of exemplary embodiments with reference to the attached drawings.

DESCRIPTION OF THE EMBODIMENTS

Figure 1:
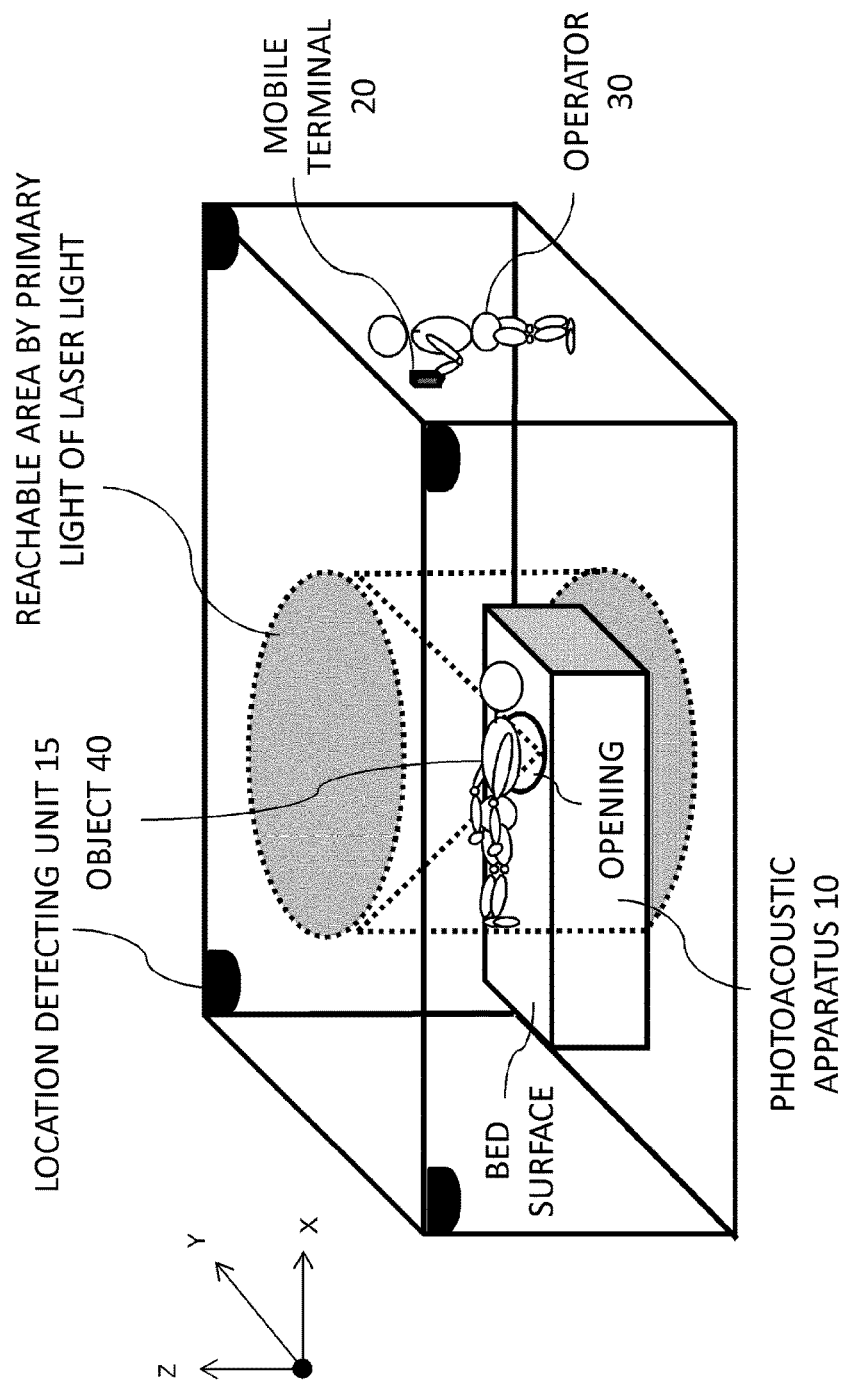
FIG. 1 is an external view of a photoacoustic apparatus according to a first embodiment.

Hereinafter, embodiments of the present invention will be described in detail with reference to the drawings. It should be noted that same components are generally assigned same reference numerals and a description thereof will be omitted. In addition, it is to be understood that dimensions, materials, shapes, relative arrangements, and the like of parts used in the description of the embodiments are intended to be changed as deemed appropriate in accordance with configurations and various conditions of apparatuses to which the present invention is to be applied and are not intended to limit the scope of the present invention.

First Embodiment

A photoacoustic apparatus according to the present embodiment is an apparatus which irradiates an object with pulse light and, by receiving and analyzing photoacoustic waves generated inside the object due to the pulse light, visualizes or, in other words, creates images of characteristic information relating to optical characteristics inside the object.

Characteristic information relating to optical characteristics generally refer to a distribution of generation sources or a distribution of initial sound pressure of acoustic waves, a distribution of optical energy absorption, a distribution of absorption coefficients, or a distribution of characteristics related to a concentration of a substance constituting tissue in an object. Examples of a distribution of characteristics related to concentration include distributions of oxygen saturation, a value obtained by weighting oxygen saturation with intensity of an absorption coefficient or the like, total hemoglobin concentration, oxyhemoglobin concentration, and deoxyhemoglobin concentration. In addition, a distribution of characteristics related to concentration may be a distribution of glucose concentration, collagen concentration, melanin concentration, or a volume fraction of fat or water.

Moreover, an acoustic wave according to the present embodiment is typically an ultrasonic wave and includes an elastic wave which is also referred to as a sonic wave, an ultrasonic wave, an acoustic wave, a photoacoustic wave, or an optical ultrasonic wave. In addition, an acoustic wave generated by a photoacoustic effect is referred to as a photoacoustic wave or an optical ultrasonic wave. Furthermore, in the present invention, light includes electromagnetic waves such as visible light and infrared light. Light with a specific wavelength can be appropriately selected according to a component set as a measurement object of the apparatus.

<System Configuration>

A configuration of a photoacoustic apparatus according to the first embodiment will be described.

Figure 2:
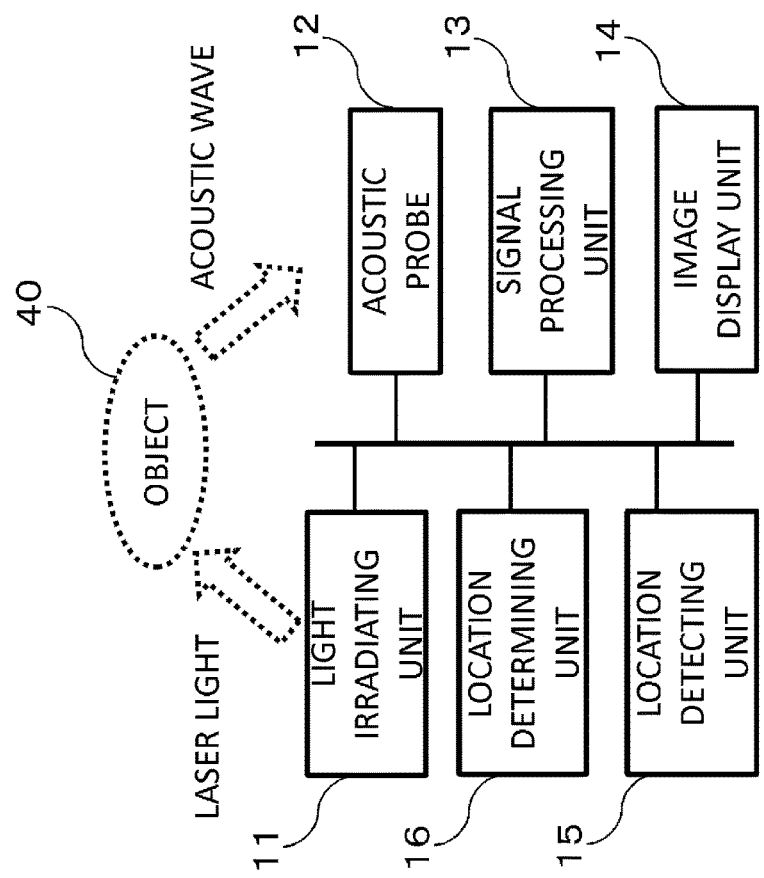
FIG. 2 is a system configuration diagram of the photoacoustic apparatus according to the first embodiment.

FIG. 1 is an external view of the photoacoustic apparatus according to the first embodiment, and FIG. 2 is a system configuration diagram of the photoacoustic apparatus according to the first embodiment.

A photoacoustic apparatus 10 according to the present embodiment includes a light irradiating unit 11, an acoustic probe 12, a signal processing unit 13, an image display unit 14, a location detecting unit 15, and a location determining unit 16.

In addition, a mobile terminal 20 is a terminal held by an operator 30 of the apparatus and is equipped with a function for communicating with the location determining unit 16 included in the photoacoustic apparatus 10 and a function for presenting acquired information to the operator.

In the first embodiment, an object 40 is a human breast. The photoacoustic apparatus 10 according to the present embodiment is a bed-type apparatus having an opening, in which measurements are performed in a state where an examinee is lying down in a prone position on a bed surface in an upper part of the apparatus and abreast is inserted into the opening provided in the upper part.

Figure 3:
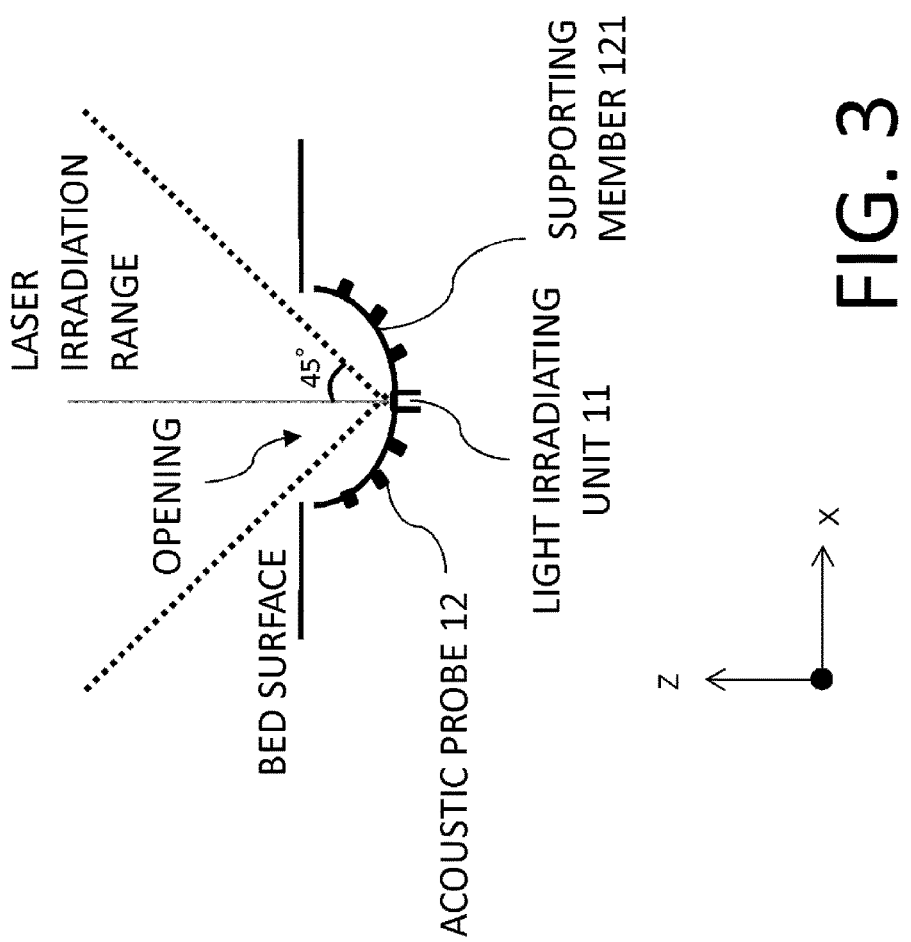
FIG. 3 is a sectional view of the photoacoustic apparatus according to the first embodiment.

The light irradiating unit 11 and the acoustic probe 12 are arranged inside the opening. FIG. 3 is an X-Z sectional view of the apparatus at the opening. A supporting member 121 which is a hemispherical member is arranged in the opening of the apparatus, and the light irradiating unit 11 and the acoustic probe 12 are arranged on an inner surface of the supporting member 121. As shown in FIG. 2, the inserted breast is irradiated by laser light from the light irradiating unit 11 and the acoustic probe 12 receives acoustic waves created inside the breast. Subsequently, the signal processing unit 13 processes a signal output by the acoustic probe and generates an image. The generated image is output to and displayed by the image display unit 14.

Hereinafter, the respective units constituting the photoacoustic apparatus according to the present embodiment will be described.

<<Light Irradiating Unit 11>>

The light irradiating unit 11 is a unit which is configured to irradiate an object with laser light (pulse light) and which is constituted by a light source and an optical member.

While the light source is desirably a laser light source in order to obtain a large output, a light-emitting diode, a flash lamp, or the like may be used in place of a laser. When using a laser as the light source, various lasers such as a solid-state laser, a gas laser, a dye laser, and a semiconductor laser can be used. Timings, waveforms, intensity, and the like of irradiation are controlled by a light source control unit (not shown). The light source control unit may be integrated with the light source. While an alexandrite laser is used in the present embodiment, a YAG laser, a titanium sapphire laser, and the like, may be used instead.

In addition, desirably, a wavelength of the pulse light is a specific wavelength which is absorbed by a specific component among components constituting the object and which enables light to propagate to the inside of the object. Specifically, when the object is a living organism, light with a wavelength of 650 nm or more and 1100 nm or less is desirably used. Moreover, when oxygen saturation is acquired as object information, two or more wavelengths may be used.

Furthermore, in order to effectively generate a photoacoustic wave, light must be irradiated in a sufficiently short period of time in accordance with thermal characteristics of the object. When the object is a living organism, a pulse width of the generated pulse light is preferably around 10 to 50 nanoseconds.

Moreover, while the example shown in FIG. 3 is configured such that pulse light is directly irradiated from the light irradiating unit 11, only an emitting end may be arranged on a bottom surface of the supporting member. In this case, the pulse light generated by the light source irradiates the object from the emitting end via an optical member such as a lens, a mirror, a diffuser plate, or an optical fiber.

Moreover, in the present embodiment, the pulse light is isotropically irradiated at an angle of 45 degrees as shown in FIG. 3. In addition, the supporting member 121 is configured so as to be independently movable by a scanning mechanism (not shown) from the bed surface holding the examinee and is capable of irradiating pulse light while changing positions relative to the object. For example, a trajectory along which the supporting member 121 is moved can have a spiral shape. Moreover, a direction of movement may be a planar direction or a rotation direction.

In addition, while light irradiation is controlled by the light source control unit (not shown) in the present embodiment, this configuration is not restrictive. For example, light irradiation may be controlled by a processor inside the mobile terminal 20.

<<Acoustic Probe 12>>

The acoustic probe 12 is a unit which is configured to detect an acoustic wave arriving from inside an object and to convert the acoustic wave into an analog electrical signal. The probe is also referred to as an acoustic probe, an acoustic detector, or a transducer. As the probe, any kind of probe may be used including those using a piezoelectric phenomenon, optical resonance, or a variation in capacitance.

Since acoustic waves generated by a living organism are ultrasonic waves from 100 kHz to 100 MHz, an element capable of receiving this frequency band is used as the acoustic probe 12. Specifically, a transducer using a piezoelectric phenomenon, a transducer using optical resonance, a transducer using a variation in capacity, or the like can be used.

In addition, desirably, an acoustic probe having a high receiving sensitivity and a wide frequency band is used. Specific examples of the acoustic probe include a piezoelectric element using lead zirconatetitanate (PZT) or the like, a capacitive micromachined ultrasonic transducer (CMUT), and a probe using a Fabry-Perot interferometer. However, the acoustic probe is not limited to these examples and any probe may be used as long as functions as a probe are satisfied.

Furthermore, the acoustic probe may be an arrangement of a plurality of acoustic elements. Simultaneously receiving acoustic waves at a plurality of positions enables measurement time to be shortened and an effect of vibration of the object and the like to be reduced.

In the present embodiment, an acoustic probe is formed by providing the illustrated hemispherical supporting member 121 and arranging a plurality of acoustic elements on an inner surface of the supporting member 121.

<<Signal Processing Unit 13>>

The signal processing unit 13 is a unit which is configured to amplify the analog electrical signal output by the acoustic probe 12 and to convert the analog electrical signal into a digital signal. The signal processing unit 13 is typically constituted by an amplifier, an A/D converter, a field programmable gate array (FPGA) chip, or the like. When a plurality of signals are obtained from the acoustic probe 12, desirably, a plurality of signals can be processed simultaneously.

In addition, the signal processing unit 13 is also a unit configured to process a digitally-converted signal (hereinafter, a photoacoustic signal) and to reconstruct an image representing characteristic information inside the object (a characteristic information acquiring unit according to the present invention). While methods of reconstruction include a Fourier transform method, a universal back-projection method (UBP method), and a filtered back-projection method, any method may be used.

In addition, a configuration may be adopted in which functional information (such as oxygen saturation) inside the object is calculated by processing a photoacoustic signal obtained through irradiation of irradiation light with a plurality of wavelengths.

<<Image Display Unit 14>>

The image display unit 14 is a unit which is configured to display the image output from the signal processing unit 13. For example, a liquid crystal display, a plasma display, an organic EL display, an FED, or the like can be used as a display apparatus. Moreover, the display apparatus may be provided separate from the photoacoustic apparatus. For example, acquired object information may be transmitted to an external display apparatus in a wired or wireless manner.

<<Location Detecting Unit 15 and Mobile Terminal 20>>

The location detecting unit 15 is a unit which is configured to acquire a location of an operator (hereinafter, an operator location) relative to the apparatus. In addition, the mobile terminal 20 is a small computer held by the operator (for example, a physician or a technician) of the photoacoustic apparatus 10.

In the present embodiment, the location detecting unit 15 is a location receiver which detects a location of a target (the mobile terminal 20) using an RFID system and which outputs coordinates of the location.

The location receiver constituting the location detecting unit 15 is arranged at four corners of a room in which the photoacoustic apparatus 10 is installed. The mobile terminal 20 includes an RFID tag and a receiver having received a transmitted signal detects a location of the mobile terminal 20. Moreover, while the location of the mobile terminal 20 is expressed by a coordinate system with the room in which the photoacoustic apparatus 10 is installed as a reference in the present embodiment, this configuration is not necessarily restrictive.

Figure 4:
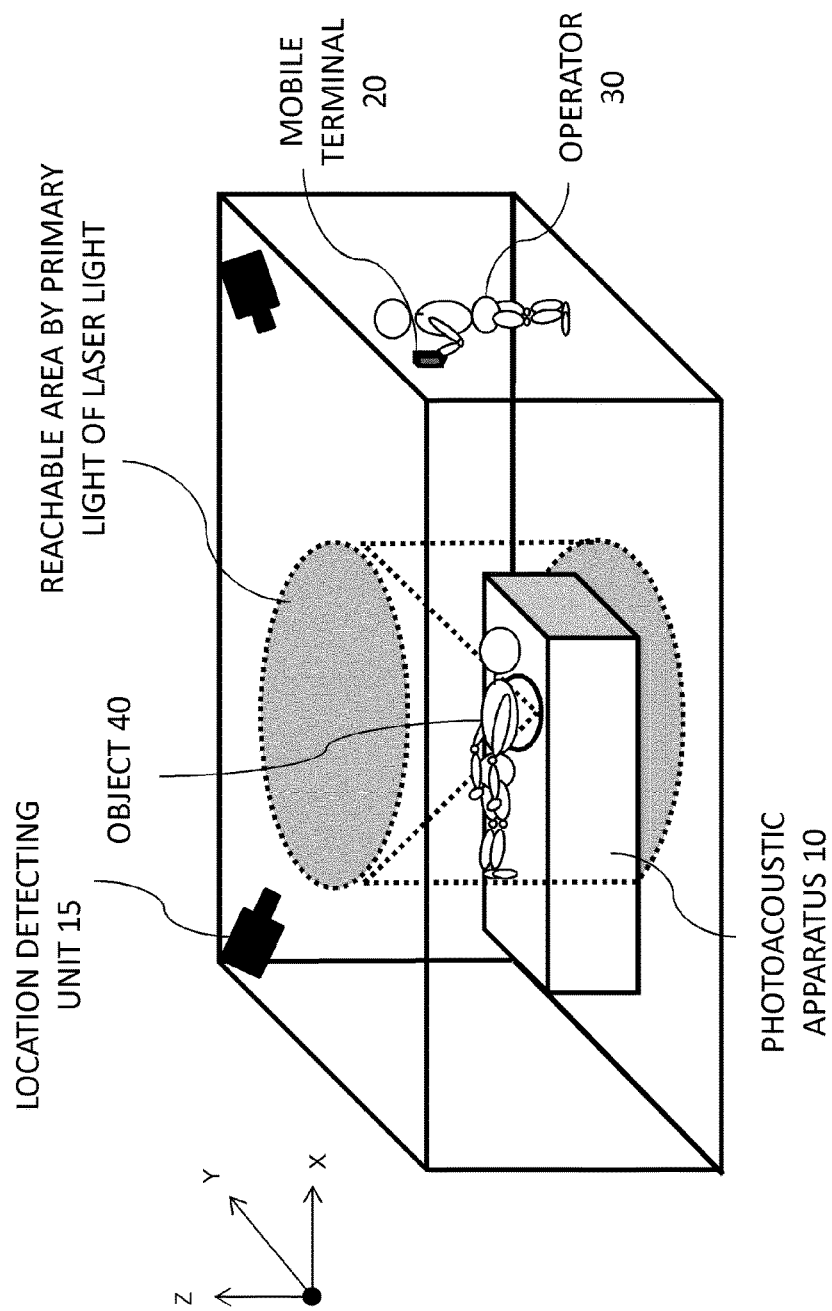
FIG. 4 is a diagram for explaining a modification of a location detecting unit.
Figure 5:
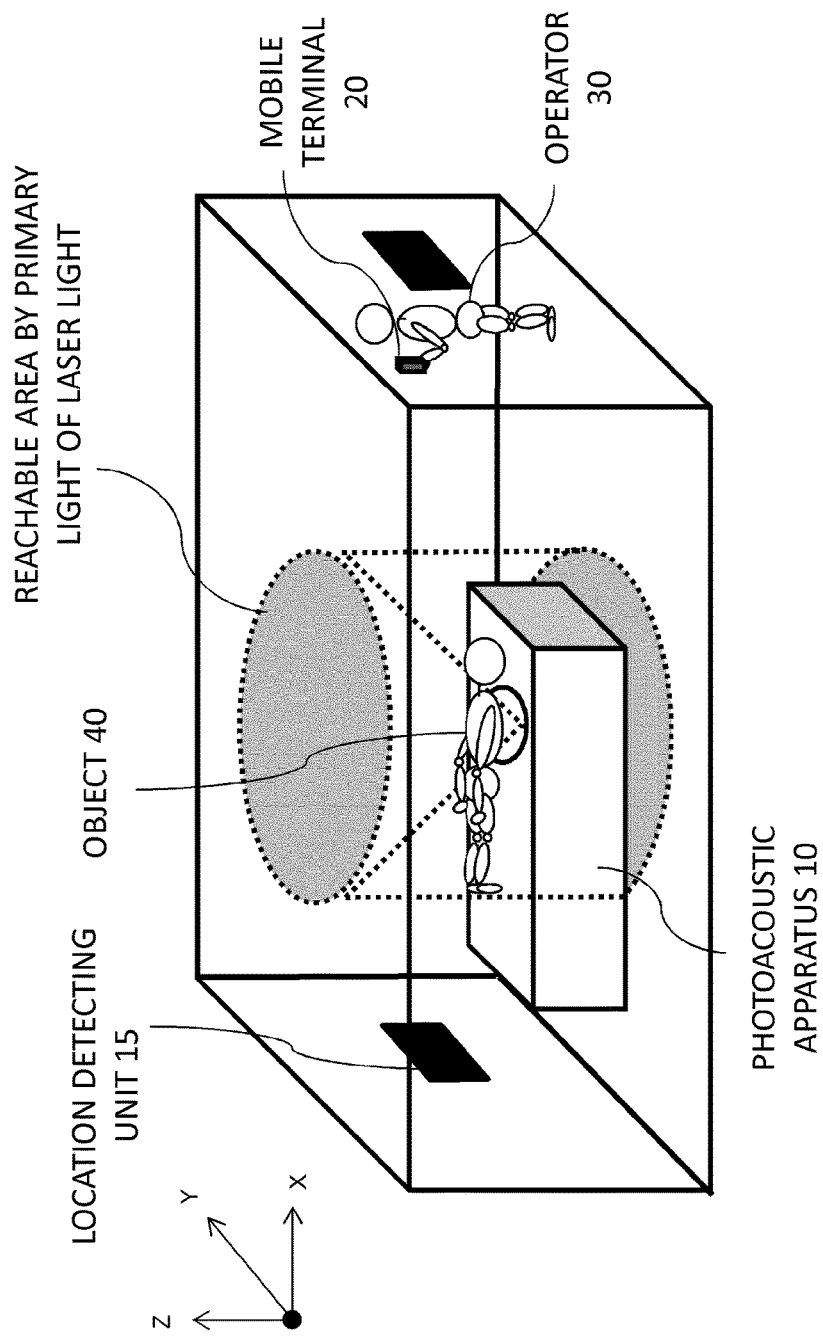
FIG. 5 is a diagram for explaining a modification of a location detecting unit.

Moreover, the location detecting unit 15 may use a camera such as that shown in FIG. 4 and detect an operator location based on an acquired camera image (in this case, the mobile terminal 20 is not necessary required). In addition, an antenna (or a sensor) arranged at a location such as that shown in FIG. 5 can be used as the location detecting unit 15.

Alternatively, an operator location may be detected using a beacon or an infrared sensor. A LAN card or an LED marker can also be used instead of the RFID tag. Alternatively, a location of the mobile terminal may be detected using GPS, a Wi-Fi™ network, or a Bluetooth™ network. When using GPS, a location of the mobile terminal is determined based on latitude and longitude information. In this case, the operator location can be identified by registering, in advance, latitude and longitude information on the room in which the photoacoustic apparatus 10 is installed. Moreover, in the present embodiment, an error of the operator location obtained by the location detecting unit is favorably kept to several 10 cm or less and more favorably kept to several cm and less. In this case, a beacon or a location receiver is favorably adopted as the location detecting unit.

Moreover, when a beacon is used, the mobile terminal 20 may receive a radio wave transmitted from the beacon and the mobile terminal 20 may calculate and transmit its own location. A combination of the location detecting unit 15 and a method of detecting a location can be selected as appropriate.

In addition, while an operator location is expressed by coordinates of the mobile terminal in the present embodiment, the operator location may be expressed using coordinates other than those of the terminal. For example, coordinates of a representative point of the body (a location of a center of gravity point or the eyes) of the operator may be used.

Furthermore, the operator location need not necessarily be expressed by a point. For example, when an area (or an approximate area) where the body of the operator is present can be acquired two-dimensionally or three-dimensionally by means such as a camera or a sensor, the operator location can be expressed by information of the area (or the approximate area).

In addition to the functions described above, the mobile terminal 20 has a function of receiving and notifying the operator of a determination result generated by the location determining unit 16 to be described later. While the mobile terminal 20 is typically a portable computer such as a tablet PC, a mobile phone, a watch or other devices may be used instead. In addition, the mobile terminal 20 may partially assume the role of the photoacoustic apparatus 10 and perform the control and the location determining function thereof.

<<Location Determining Unit 16>>

The location determining unit 16 is a unit which is configured to compare the operator location acquired by the location detecting unit 15 with area information set in advance and to transmit a comparison result to the mobile terminal 20.

In the present embodiment, the location determining unit 16 stores information on an area (hereinafter, a light reachable area) which is reachable by primary light of the pulse light irradiated from the light irradiating unit 11 (an area information acquiring unit according to the present invention). In addition, the location determining unit 16 determines whether or not location information of the mobile terminal 20 as acquired by the location detecting unit 15 is within the light reachable area (a determining unit according to the present invention). A determination result is transmitted to the mobile terminal 20.

In the present embodiment, a maximum reachable range of the primary light on a ceiling of the room and a columnar three-dimensional area obtained by drawing down the range in a vertical direction to a floor are defined as the light reachable area. For example, let us consider a case where pulse light is emitted in a spiral direction at a maximum angle of 45 degrees around an emitting end of the light irradiating unit. In this case, for example, when a height from the emitting end to the ceiling of the room is 1.5 meters, primary light reaches a range with a radius of 1.5 meters around the emitting end on the ceiling. In other words, the light reachable area is a columnar area obtained by projecting the range toward the floor in the vertical direction.

Moreover, while the location determining unit 16 is assumed to be an independent personal computer in the present embodiment, when the photoacoustic apparatus 10 is controlled by a computer, hardware may be used in combination. Alternatively, an apparatus other than a personal computer may be used. In addition, the location detecting unit 15 may be equipped with the functions of the location determining unit 16.

The location determining unit 16 determines whether or not the operator location (in other words, coordinates of the mobile terminal 20) and the light reachable area overlap each other or, in other words, whether or not the operator location is included in the light reachable area, and transmits a determination result to the mobile terminal 20.

In this case, when the operator location and the light reachable area overlap each other, the location determining unit 16 determines that at least a part of the operator's body is within the light reachable area.

Moreover, when determining overlapping, coordinates may be simply compared with each other or a location or an area where the operator is present may be assumed based on acquired coordinates and the assumed area may be compared with the light reachable area. For example, the operator may be assumed to be present in a range with a radius of 50 cm around a location of the mobile terminal 20 as acquired by the location detecting unit 15, and a determination may be made on whether or not the range overlaps with the light reachable area set in advance. In other words, an area with a radius of 50 cm around the location of the mobile terminal 20 may be considered the operator location. Accordingly, a reliable determination can be made even when accuracy of location detection is not high.

Alternatively, when the operator location is expressed by two-dimensional or three-dimensional information, a determination may be made on whether or not at least a part of the operator's body is inside the light reachable area. In addition, since a part of the operator's body with lowest MPE is the retina, a location of the eyes may be estimated using a known method and a determination may be made on whether or not the estimated location of the eyes is within the light reachable area.

<Notification Method of Determination Result>

Next, a method of issuing notification on a result of a determination performed by the location determining unit 16 will be described.

In the present embodiment, a communicating unit provided in the location determining unit 16 transmits a determination result to the mobile terminal 20, and the mobile terminal 20 causes the determination result to be displayed on a display of the mobile terminal 20. Moreover, when the mobile terminal 20 is not used, the determination result may be displayed on a PC display, a television, or a monitor. More favorably, the notification is only made to the operator so as not to give the examinee cause for anxiety. In the present embodiment, only the operator is notified of the determination result by displaying a message on a monitor of the mobile terminal 20 held by the operator. In this case, a display as a display unit also functions as a notifying unit.

Figure 6:
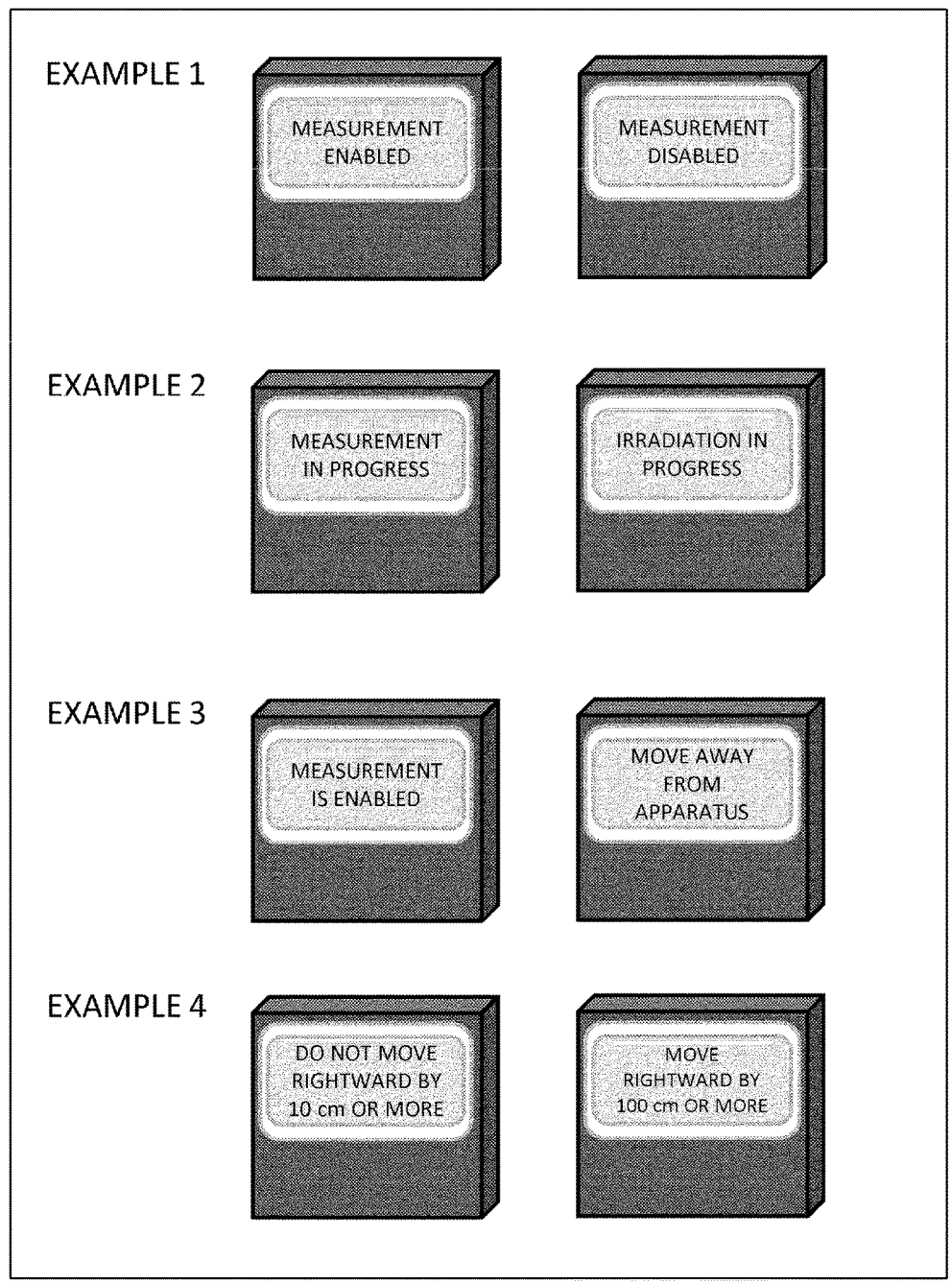
FIG. 6 is a diagram for explaining an example of a message displayed on a mobile terminal.

An example of a message displayed on the mobile terminal 20 is shown in FIG. 6. Favorably, for example, the message simply indicates whether a measurement can be performed or not. Alternatively, a status such as "measurement in progress" or "irradiation in progress" may be displayed. The fact that measurement cannot be started or a suggestion that the operator should move away from the apparatus may be displayed instead. Alternatively, for example, a direction of the light reachable area, a distance until entering the light reachable area, or a direction of movement or a movement distance in order to exit the light reachable area may be displayed.

Instead of displaying a message, a determination result may be notified by causing the mobile terminal 20 to vibrate. In this case, the mobile terminal 20 itself may be vibrated or another device worn or carried by the operator may be vibrated. Alternatively, the operator may be notified with both message display and vibration. Sound may also be used in combination. Besides the above, any means of notification may be adopted as long as the operator can be notified of a determination result.

Moreover, when the mobile terminal 20 has a function for controlling light irradiation, a button or an icon for starting laser irradiation may be displayed on the mobile terminal and irradiation may be started in accordance with an operation of the button or the icon. In this case, a specification may be adopted in which, when it is determined that the operator location is within the light reachable area, the button or the icon is grayed out to prevent irradiation from being started.

Alternatively, a determination result may be displayed on a monitor installed near the feet of the examinee. By adopting such a configuration, only the operator can be notified of the determination result.

<Process Flow>

Figure 7:
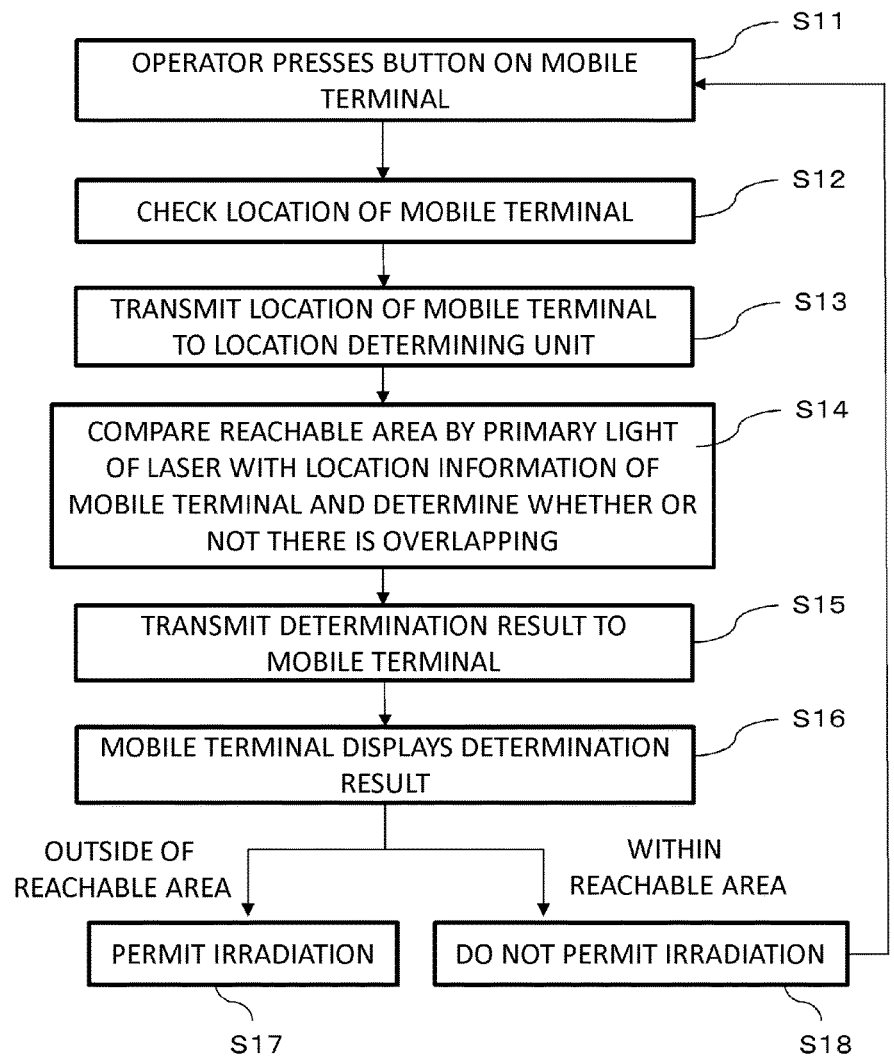
FIG. 7 is a flow chart of processes performed by the photoacoustic apparatus according to the first embodiment.

Next, a process flow chart of the photoacoustic apparatus according to the present embodiment is shown in FIG. 7.

While a mode in which the mobile terminal 20 has a function of controlling light irradiation will be described below, the process flow chart may also be applied to other modes.

When the operator presses an irradiation start button displayed on a screen of the mobile terminal 20, the processes are started (step S11).

Next, a location receiver that is the location detecting unit 15 checks a location of the mobile terminal 20 to which an RFID tag is attached (step S12). When the tag is recognized, the location detecting unit 15 determines coordinates of the mobile terminal based on a location of the tag and transmits the coordinates to the location determining unit 16 (step S13).

Next, the location determining unit 16 compares a light reachable area stored in advance and the coordinates of the mobile terminal transmitted from the location detecting unit with each other and determines whether or not the light reachable area and the coordinates overlap each other (step S14). A determination result is transmitted to and displayed by the mobile terminal (steps S15 and S16).

At this point, when the operator location is outside of the light reachable area, irradiation of laser light is permitted and irradiation is started (step S17). On the other hand, when the operator location is within the light reachable area, irradiation of laser light is not performed (step S18) and the process returns to step S11. In this case, the operator relocates and once again performs an operation for starting irradiation. In other words, the light irradiating unit 11 does not permit irradiation of light when the operator location is included in a reachable area of the light.

According to the first embodiment, a measurement of an object can be started only when an operator of the apparatus is outside of an area which may be reached by primary light of laser light. In other words, irradiation of the laser light outside of an examinee can be prevented. In addition, since the examinee is not notified of a determination result, an effect of not giving the examinee unnecessary cause for anxiety is produced.

Moreover, while the processes shown in FIG. 7 are executed when the operator performs an operation for starting a measurement in the first embodiment, determinations may be repetitively performed during a measurement and irradiation of pulse light may be stopped immediately when it is determined that the operator is within the light reachable area.

Second Embodiment

In the first embodiment, when the operator is within a light reachable area, the fact that the operator is within the light reachable area is notified and control is performed so as not to irradiate laser light. In contrast, in the second embodiment, irradiation of laser light is conditionally permitted in consideration of maintenance of the apparatus.

A configuration of a photoacoustic apparatus according to the second embodiment is similar to that of the first embodiment with the exception of the process described below.

In maintenance of the photoacoustic apparatus, operations of the light irradiating unit and the acoustic probe must be checked in a state where an object is absent. In addition, during the operation check, there may be cases where pulse light must be irradiated even when an operator (a maintenance person) of the apparatus is within the light reachable area.

In consideration thereof, in the second embodiment, control is performed so as to enable irradiation of pulse light on condition that use of protective gear is confirmed even when an operator location is within the light reachable area.

Figure 8:
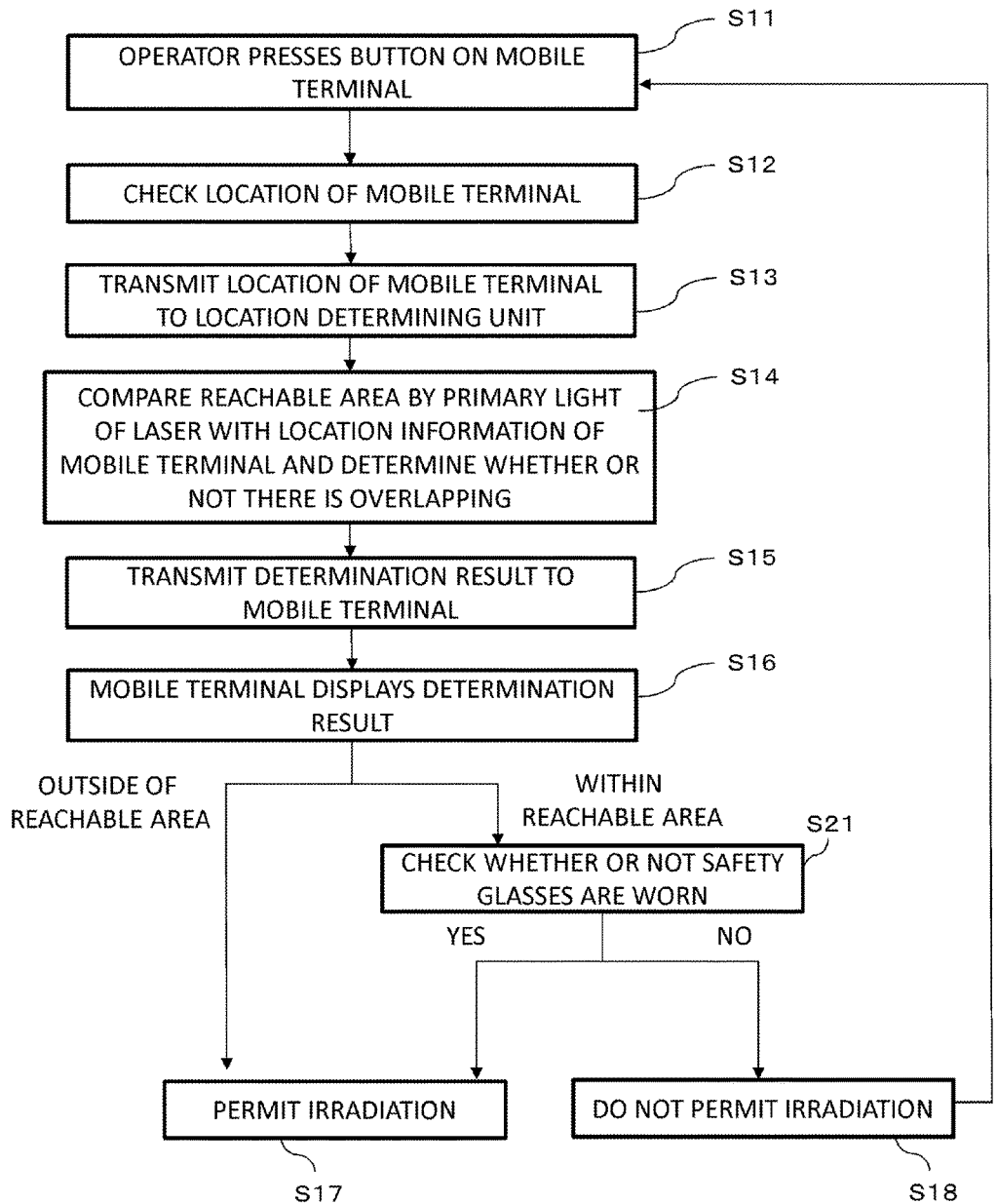
FIG. 8 is a flow chart of processes performed by the photoacoustic apparatus according to the second embodiment.

The photoacoustic apparatus according to the second embodiment is configured so as to be switchable to a maintenance mode (a second mode according to the present invention) which differs from an ordinary mode (a first mode according to the present invention: hereinafter, a user mode). FIG. 8 shows a process flow chart in the maintenance mode.

In the maintenance mode, when it is determined that the operator location is within the light reachable area, step S21 for determining whether or not protective gear (in the present example, safety glasses) is worn is executed.

Processes performed in the user mode is as shown in FIG. 7. In other words, step S21 is not executed in the user mode.

In the second embodiment, when issuing notification on a determination result in step S16, a message prompting use of safety glasses is displayed. In addition, in step S21, a message for confirming whether safety glasses are worn is displayed and a user is asked to select either Yes or No using an input unit. As the input unit, a mouse, a keyboard, a touch panel mounted to the mobile terminal 20, or the like can be adopted.

At this point, irradiation of light is started when Yes is selected while the process of step S11 and thereafter is performed once again when No is selected. In other words, irradiation of light is not permitted when safety glasses are not worn.

As described above, in the second embodiment, since irradiation of pulse light irradiation is conditionally permitted even when an operator of the apparatus is within an area which may be reached by primary light, convenience when performing maintenance is improved.

Moreover, switching between the user mode as the first mode and the maintenance mode as the second mode may be performed based on an instruction from the mobile terminal 20 or may be performed by an apparatus main body. In addition, the photoacoustic apparatus may be automatically switched to the maintenance mode when a part of the apparatus is removed.

In the present example, the operator is asked to select whether safety glasses are worn or not. Alternatively, in step S21, whether or not safety glasses are worn may be automatically detected and control may be performed based on a detection result. For example, when the location detecting unit 15 includes a camera, a face of a person and whether or not safety glasses are worn may be detected by analyzing an image. Alternatively, the camera may be provided in a unit independent of the location detecting unit 15. For example, the camera may be built into the mobile terminal 20. In this case, the operator may be asked to have his or her own face recognized using the built-in camera. In this case, the camera which photographs the operator's face and a processor which analyzes a camera image function as a detecting unit which detects whether or not the operator wears safety glasses. Moreover, at this point, a camera image used to determine an operator location may also be used to determine whether or not safety glasses are worn.

Alternatively, the safety glasses may include a contact sensor constituted by a pressure sensor or the like, and a determination that the safety glasses are worn may be made when the contact sensor detects that the operator and the safety glasses have come into contact with each other. In this case, the contact sensor functions as a detecting unit which detects whether or not the operator wears safety glasses.

(Modification)

It is to be understood that the descriptions of the respective embodiments merely represent examples of the present invention and, as such, the present invention can be implemented by appropriately modifying or combining the embodiments without departing from the spirit and the scope of the invention.

For example, the present invention may be implemented as an object information acquiring apparatus which includes at least a part of the processes described above. The present invention may also be implemented as an object information acquiring method which includes at least a part of the processes described above. The present invention may also be implemented as an information processing apparatus which determines whether or not laser light is being irradiated in combination with an object information acquiring apparatus. The present invention may also be implemented as an information processing method performed by the information processing apparatus. The processes and units described above may be implemented in any combination insofar as technical contradictions do not occur.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-033354, filed on Feb. 24, 2016, which is hereby incorporated by reference herein in its entirety.

What is claimed is:

1. An object information acquiring apparatus, comprising:
   a light irradiating unit configured to irradiate an object with light;
   an acoustic probe configured to receive an acoustic wave generated from the object due to the light and to convert the acoustic wave into an electrical signal;
   a characteristic information acquiring unit configured to acquire characteristic information relating to the object based on the electrical signal;
   an area information acquiring unit configured to acquire information relating to a reachable area of the light irradiated from the light irradiating unit;
   a location detecting unit configured to acquire an operator location which is a location of an operator; and
   a determining unit configured to determine whether the operator location is in a first state where the operator location overlaps with the reachable area of the light or a second state where the operator location does not overlap with the reachable area of the light.

2. The object information acquiring apparatus according to claim 1, wherein
   the light irradiating unit is configured not to permit irradiation of light when the operator location is in the first state, based on a determination result of the determining unit.

3. The object information acquiring apparatus according to claim 1, wherein
   the light irradiating unit is configured to perform switching between
   a first mode in which irradiation of light is not permitted when the operator location is in the first state, based on a determination result of the determining unit and
   a second mode in which irradiation of light is permitted even when the operator location is in the first state, based on a determination result of the determining unit.

4. The object information acquiring apparatus according to claim 3, further comprising
   an input unit configured to accept an input regarding whether or not the operator wears safety glasses, wherein
   the light irradiating unit is configured to permit irradiation of light in the second mode on condition that information indicating that the safety glasses are worn is acquired from the input unit.

5. The object information acquiring apparatus according to claim 4, wherein
   the input unit is configured to prevent an input regarding whether or not the operator wears safety glasses when the light irradiating unit is in the first mode.

6. The object information acquiring apparatus according to claim 3, further comprising
   a detecting unit configured to detect whether or not the operator wears safety glasses, wherein
   the light irradiating unit is configured to permit irradiation of light in the second mode on condition that the detecting unit detects that the safety glasses are worn.

7. The object information acquiring apparatus according to claim 6, wherein
   the light irradiating unit is configured to permit irradiation of light in the first mode, based on a determination result of the determining unit regardless of a detection result of the detecting unit.

8. The object information acquiring apparatus according to claim 6, wherein
the location detecting unit is configured to acquire the operator location from a camera image, and
the detecting unit is configured to detect whether or not the operator wears safety glasses, based on the camera image.

9. The object information acquiring apparatus according to claim 1, further comprising
a notifying unit configured to perform a notification for prompting the use of safety glasses.

10. The object information acquiring apparatus according to claim 1, further comprising
a notifying unit configured to issue notification on a determination result of the determining unit.

11. The object information acquiring apparatus according to claim 1, wherein
the operator location is a location corresponding to at least a part of the operator's body.

12. The object information acquiring apparatus according to claim 1, wherein
the location detecting unit is configured to estimate a location of the eyes of the operator and consider the estimated location of the eyes as the operator location.

13. The object information acquiring apparatus according to claim 1, wherein
the location detecting unit is configured to acquire the operator location, based on information received from a terminal carried by the operator.

14. The object information acquiring apparatus according to claim 1, wherein
the location detecting unit is configured to include one or more beacons and to acquire the operator location by receiving, from a terminal carried by the operator, location information generated based on a signal transmitted from the beacon.

15. A control method for an object information acquiring apparatus including a light irradiating unit which irradiates an object with light and an acoustic probe which receives an acoustic wave generated from the object due to the light and which converts the acoustic wave into an electrical signal, the control method comprising:
acquiring characteristic information relating to the object, based on the electrical signal;
acquiring information relating to a reachable area of the light irradiated from the light irradiating unit;
acquiring an operator location which is a location of an operator; and
determining whether the operator location is in a first state of where the operator location overlaps with the reachable area of the light or a second state where the operator location does not overlap with the reachable area of the light.

16. An information processing apparatus which determines whether or not to permit irradiation of an object with light by an object information acquiring apparatus,
the information processing apparatus comprising:
an area information acquiring unit configured to acquire information relating to a reachable area of the light with which the object is irradiated;
a location detecting unit configured to acquire an operator location which is a location of an operator of the object information acquiring apparatus; and
a determining unit configured to determine whether the operator location is in a first state where the operator location overlaps with the reachable area of the light or a second state where the operator location does not overlap with the reachable area of the light.

* * * * *